United States Patent
Chou et al.

(10) Patent No.: US 9,870,614 B1
(45) Date of Patent: Jan. 16, 2018

(54) AUTOMATIC 3D BRAIN TUMOR SEGMENTATION AND CLASSIFICATION

(71) Applicant: SONY CORPORATION, Tokyo (JP)

(72) Inventors: Chen-Rui Chou, Palo Alto, CA (US); Bi Song, San Jose, CA (US); Ming-Chang Liu, San Jose, CA (US)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/218,986

(22) Filed: Jul. 25, 2016

(51) Int. Cl.
*G06T 7/00* (2017.01)
*G06K 9/62* (2006.01)
*A61B 5/055* (2006.01)
*A61B 5/00* (2006.01)
*G01R 33/48* (2006.01)

(52) U.S. Cl.
CPC ............ *G06T 7/0012* (2013.01); *A61B 5/055* (2013.01); *A61B 5/7264* (2013.01); *G01R 33/4808* (2013.01); *G01R 33/4828* (2013.01); *G06K 9/6267* (2013.01); *G06T 7/0079* (2013.01); *A61B 2576/00* (2013.01); *G06T 2200/04* (2013.01); *G06T 2207/10088* (2013.01); *G06T 2207/30016* (2013.01); *G06T 2207/30096* (2013.01)

(58) Field of Classification Search
USPC .................................................. 382/128, 173
See application file for complete search history.

(56) References Cited

U.S. PATENT DOCUMENTS

| | | | | |
|---|---|---|---|---|
| 7,876,938 | B2* | 1/2011 | Huang | G06T 7/33 382/128 |
| 8,358,818 | B2* | 1/2013 | Miga | A61B 90/36 382/128 |
| 8,571,278 | B2* | 10/2013 | Sonka | G06K 9/4638 382/128 |
| 8,908,948 | B2* | 12/2014 | Fan | G06T 7/0081 128/922 |
| 9,129,382 | B2 | 9/2015 | Fan et al. | |
| 9,159,128 | B2 | 10/2015 | Madabhushi et al. | |
| 2007/0081712 | A1* | 4/2007 | Huang | G06T 7/33 382/128 |
| 2012/0093381 | A1* | 4/2012 | Fan | G06T 7/0081 382/131 |
| 2016/0035093 | A1 | 2/2016 | Kateb et al. | |

FOREIGN PATENT DOCUMENTS

WO 2015138385 A1 9/2015
WO 2016007518 A1 1/2016

* cited by examiner

*Primary Examiner* — Ishrat I Sherali
(74) *Attorney, Agent, or Firm* — Haverstock & Owens LLP (57) ABSTRACT

A fully automatic brain tumor segmentation and classification method and system improve the healthcare experience with machine intelligence. The automatic brain tumor segmentation and classification method and system utilize whole tumor segmentation and multi-class tumor segmentation to provide accurate analysis.

29 Claims, 12 Drawing Sheets

AUTOMATIC 3D BRAIN TUMOR SEGMENTATION AND CLASSIFICATION

FIELD OF THE INVENTION

The present invention relates to tumor imaging. More specifically, the present invention relates to 3D brain tumor segmentation and classification.

BACKGROUND OF THE INVENTION

During neurosurgery, surgeons need to understand where the tumor is and the boundaries of its various components. Usually, it takes several hours for clinicians to manually contour the tumor classes from multiple pre-operative MRI scans which is a significant waste of medical resources.

SUMMARY OF THE INVENTION

A fully automatic brain tumor segmentation and classification method and system improve the healthcare experience with machine intelligence. The automatic brain tumor segmentation and classification method and system utilize whole tumor segmentation and multi-class tumor segmentation to provide accurate analysis.

In one aspect, a method programmed in a non-transitory memory of a device comprises performing whole tumor segmentation and performing multi-class tumor segmentation. The whole tumor segmentation includes: data normalization and initial segmentation. The whole tumor segmentation includes: utilizing multi-modal MRIs including T1, T1c, Flair and T2, determining a least-tumor hemisphere, classifying tissue, identifying intensity control points based on intensities of different tissue structures, normalizing the intensity for each of the MRIs based on the intensity control points, locating initial tumor seeds and segmenting a tumor based on the tumor seeds. The multi-class tumor segmentation includes: feature extraction, voxel classification and refinement. Feature extraction includes: voxel-wise features and context features, wherein voxel-wise features include determining appearance features, texture features and location features. Context feature extraction further includes: extracting a mean intensity in each octant of an MRI, extracting multiscale context features and combining the context features from a T1c MRI and a T2 MRI. Voxel classification utilizes information from the feature extraction and decision trees to classify a tumor. Refinement includes pathology-guided refinement to ensure a correct classification of the tumor.

In another aspect, an apparatus comprises a non-transitory memory for storing an application, the application for: performing whole tumor segmentation and performing multi-class tumor segmentation and a processing component coupled to the memory, the processing component configured for processing the application. The whole tumor segmentation includes: data normalization and initial segmentation. The whole tumor segmentation includes: utilizing multi-modal MRIs including T1, T1c, Flair and T2, determining a least-tumor hemisphere, classifying tissue, identifying intensity control points based on intensities of different tissue structures, normalizing the intensity for each of the MRIs based on the intensity control points, locating initial tumor seeds and segmenting a tumor based on the tumor seeds. The multi-class tumor segmentation includes: feature extraction, voxel classification and refinement. Feature extraction includes: voxel-wise features and context features, wherein voxel-wise features include determining appearance features, texture features and location features. Context feature extraction further includes: extracting a mean intensity in each octant of an MRI, extracting multi-scale context features and combining the context features from a T1c MRI and a T2 MRI. Voxel classification utilizes information from the feature extraction and decision trees to classify a tumor. Refinement includes pathology-guided refinement to ensure a correct classification of the tumor.

In another aspect, a system comprises a magnetic resonance imaging device and a computing device configured for: performing whole tumor segmentation and performing multi-class tumor segmentation. The whole tumor segmentation includes: data normalization and initial segmentation. The whole tumor segmentation includes: utilizing multi-modal MRIs including T1, T1c, Flair and T2, determining a least-tumor hemisphere, classifying tissue, identifying intensity control points based on intensities of different tissue structures, normalizing the intensity for each of the MRIs based on the intensity control points, locating initial tumor seeds and segmenting a tumor based on the tumor seeds. The multi-class tumor segmentation includes: feature extraction, voxel classification and refinement. Feature extraction includes: voxel-wise features and context features, wherein voxel-wise features include determining appearance features, texture features and location features. Context feature extraction further includes: extracting a mean intensity in each octant of an MRI, extracting multiscale context features and combining the context features from a T1c MRI and a T2 MRI. Voxel classification utilizes information from the feature extraction and decision trees to classify a tumor. Refinement includes pathology-guided refinement to ensure a correct classification of the tumor.

DETAILED DESCRIPTION OF THE PREFERRED EMBODIMENT

To expedite the process of tumor analysis, the automatic 3D brain tumor segmentation and classification method described herein is able to be implemented. There are many brain tumor segmentation challenges such as large intensity variations across subjects, unclear and irregular boundaries, and significant different tumor appearance in MRI across subject.

Figure 1:
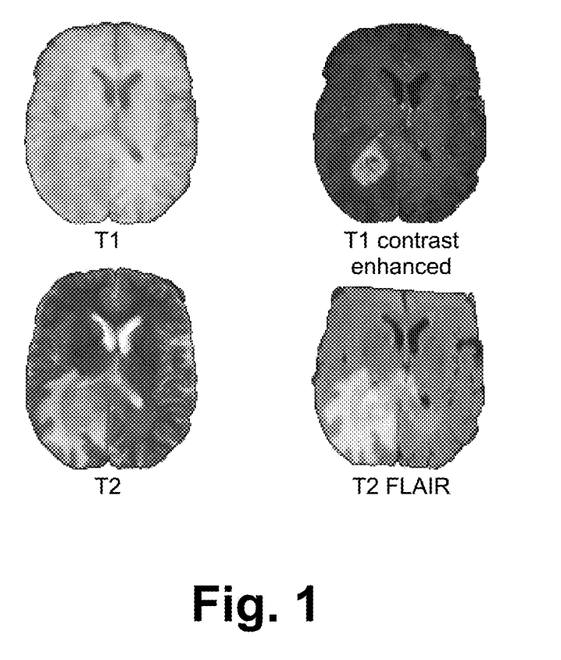
FIG. 1 illustrates multi-modal MRIs according to some embodiments.

FIG. 1 illustrates multi-modal MRIs according to some embodiments. The multi-modal MRIs include T1, T1 contrast enhanced (T1c), T2 and T2 flair.

Figure 2:
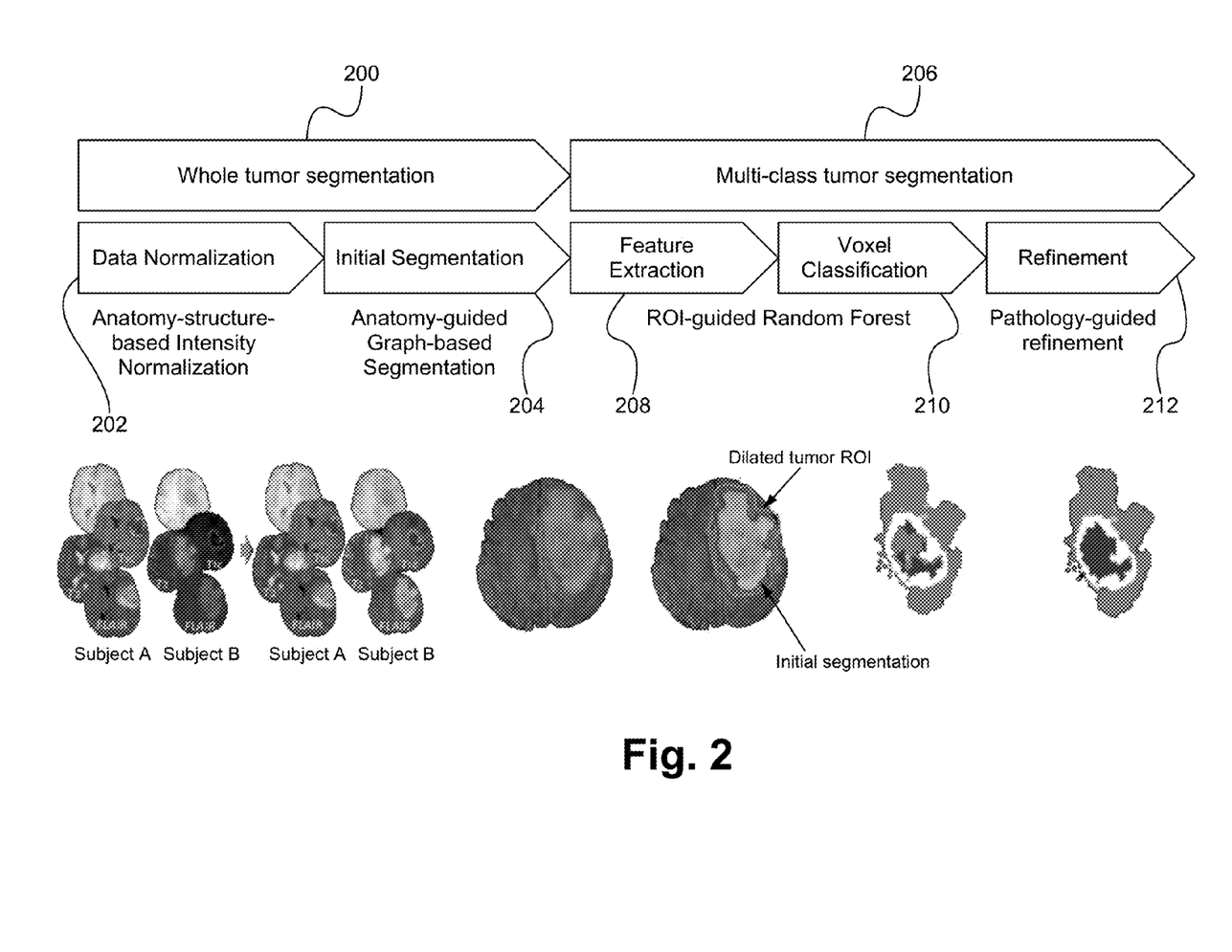
FIG. 2 illustrates a diagram of the automatic 3D brain tumor segmentation and classification method according to some embodiments.

FIG. 2 illustrates a diagram of the automatic 3D brain tumor segmentation and classification method according to some embodiments. In the step 200, whole tumor segmentation is performed. Whole tumor segmentation includes data normalization 202 and initial segmentation 204. Data normalization 202 includes anatomy-structure-based intensity normalization. Initial segmentation 204 includes anatomy-guided graph-based segmentation. In the step 206, multi-class tumor segmentation is performed. Multi-class tumor segmentation includes feature extraction 208, voxel classification 210 and refinement 212. Feature extraction 208 and voxel classification 210 involve using Region of Interest (ROI)-guided Random Forest. Refinement 212 includes pathology-guided refinement. Each of the steps is described further herein. In some embodiments, fewer or additional steps are implemented. For example, steps of acquiring the MRI information and/or displaying the refined images are able to be included. In some embodiments, the order of the steps is modified.

Unlike the CerebroSpinal Fluid (CSF)-based implementation which assumes the tumor does not affect the CSF appearance, the automatic 3D brain tumor segmentation and classification method uses part of the brain that contains no or the least amount of tumors to estimate structure intensities.

Figure 3:
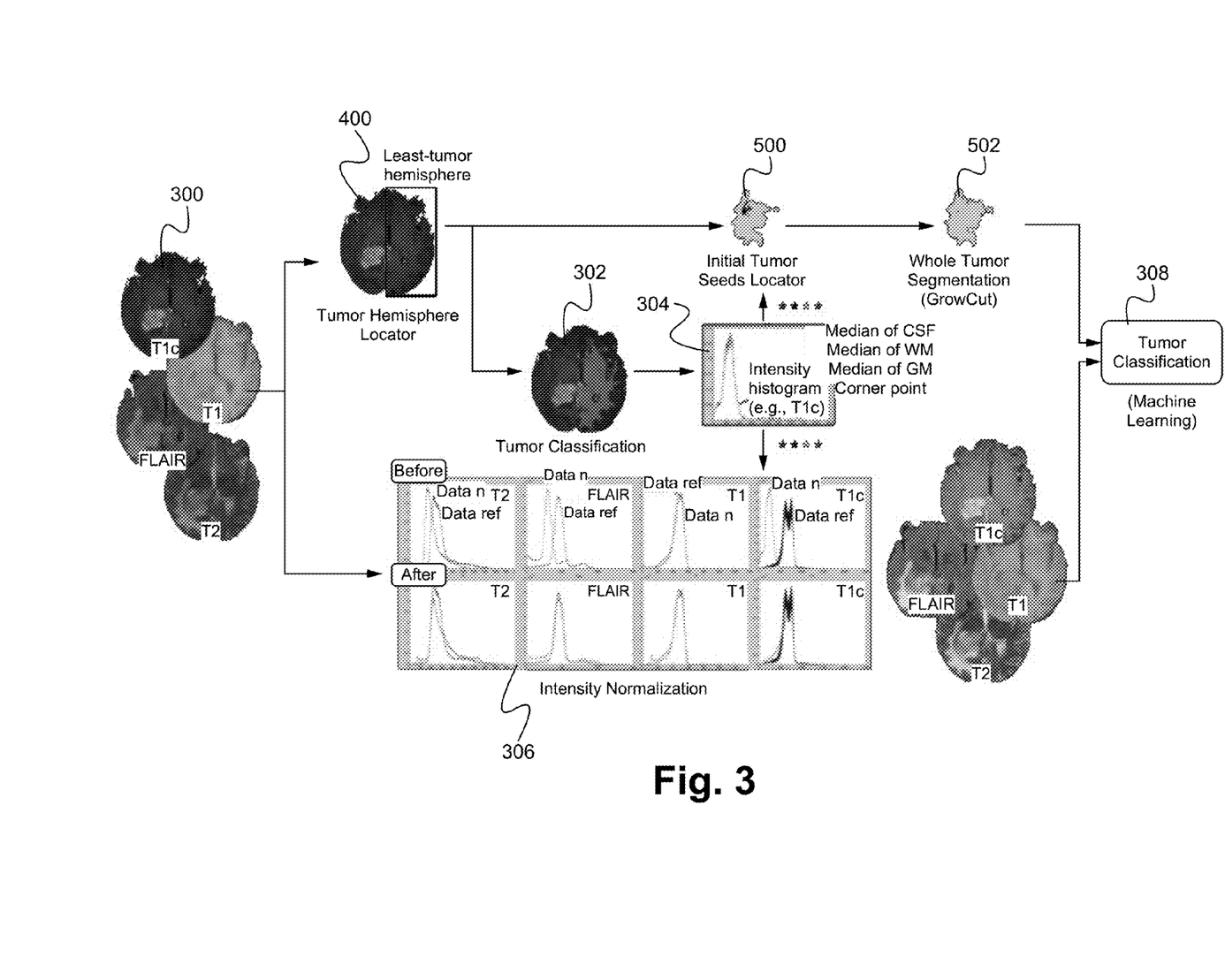
FIG. 3 illustrates a diagram of a whole tumor segmentation algorithm flow according to some embodiments.

FIG. 3 illustrates a diagram of a whole tumor segmentation algorithm flow according to some embodiments. Multi-modal MRIs 300 (e.g., T1, T1c, Flair and T2) are acquired. The T1c MRI is analyzed to determine a least-tumor hemisphere, in the step 400. Determining a least-tumor hemisphere is able to be implemented in any manner such as locating tumors in each hemisphere and then comparing the two hemispheres to determine which has fewer tumors. In another example, the hemispheres are compared with known data (e.g., hemispheres without any tumors), and the hemisphere that is less different than the known data is selected as the least-tumor hemisphere. In some embodiments, determining a least-tumor hemisphere includes determining a symmetric difference between the flair and T2 MRIs, since a tumor rarely happens completely symmetrically, then thresholding and union are performed, and the hemisphere which does not contain the center of mass is the least-tumor hemisphere. In the step 302, tissue classification is implemented to classify the brain tissue into White Matter (WM), Gray Matter (GM) and Cerebrospinal Fluid (CSF). Tissue classification is able to be implemented in any manner known to one skilled in the art. In the step 304, an intensity histogram is generated for each of the multi-modal MRIs 300 (e.g., T1, T1c, Flair, T2). In some embodiments, the intensity control points are generated from the histogram using the median of the CSF, White Matter (WM), Gray Matter (GM), and the corner point. In the step 306, intensity normalization is performed for each of the multi-modal MRIs 300 (T1, T1c, Flair, T2). Intensity normalization is able to be implemented in any manner. For example, intensities of control points of each MRI are matched. Furthering the example, the intensities of brain structures (WM, GM, CSF) are mapped to that of reference MRIs. In the step 500, initial tumor seeds are located. In some embodiments, the initial tumor seeds are located using the intensity histograms. The initial tumor seeds are able to be detected based on intensity (e.g., an intensity above a threshold is considered to be an initial tumor seed) and symmetric difference of input MRIs. In the step 502, a very fast segmentation algorithm based on the region-growing-based segmentation referred to as GrowCut is implemented for whole tumor segmentation. In some embodiments, the whole tumor segmentation is iterated for multiple tumors. In the step 308, using the whole tumor segmentation and the intensity normalization, tumor classification is performed for multi-class tumor classification. For example, machine learning is utilized to learn to recognize a tumor and/or to classify a tumor. In some embodiments, the tumor classification takes the output of the whole growth segmentation and the intensity normalization as input to classify the tumor. In some embodiments, fewer or additional steps are implemented. In some embodiments, the order of the steps is modified.

Figure 4:
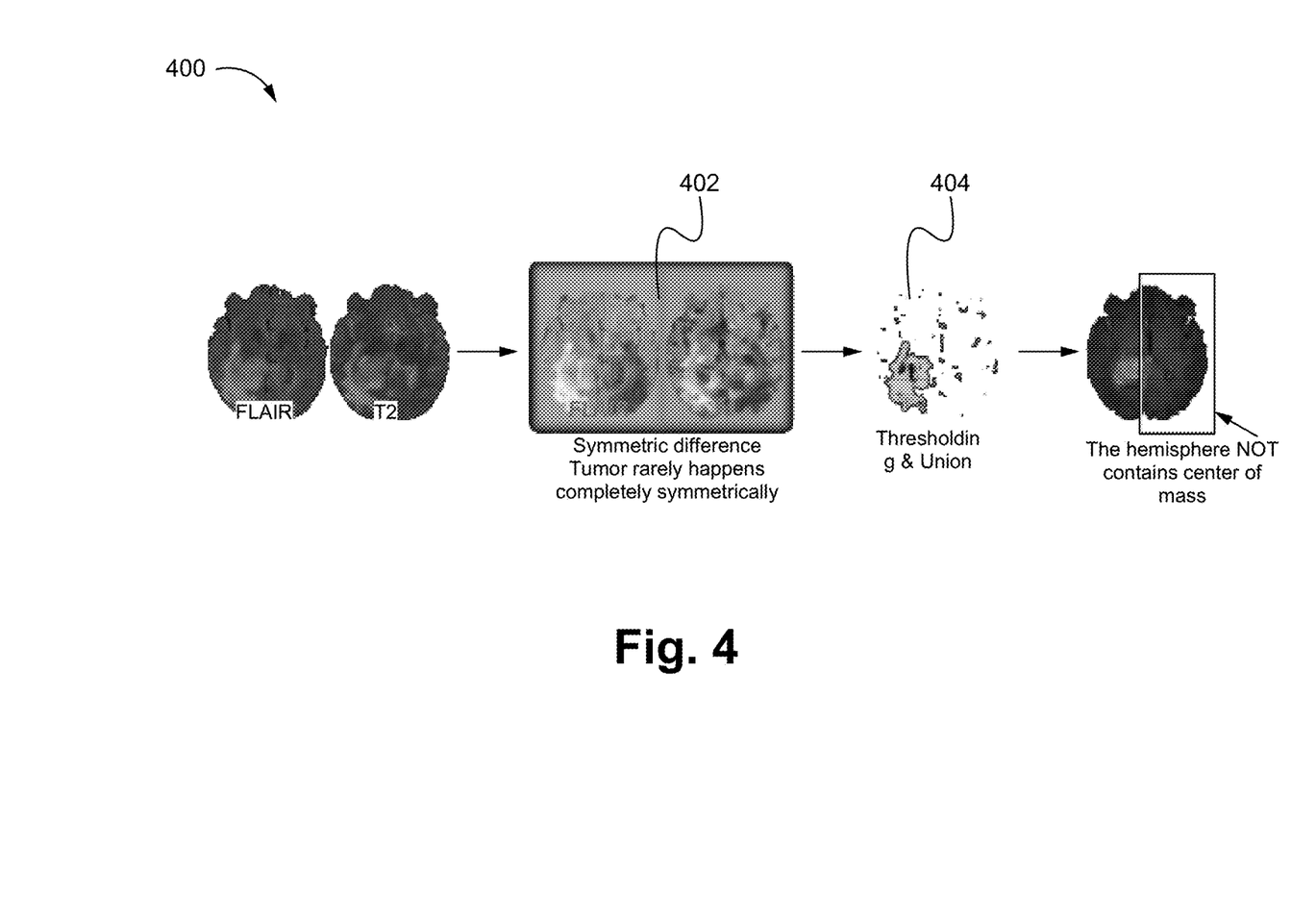
FIG. 4 illustrates a diagram of a least-tumor hemisphere locator algorithm according to some embodiments.

FIG. 4 illustrates a diagram of a least-tumor hemisphere locator algorithm according to some embodiments. Determining a least-tumor hemisphere 400 is able to be implemented in any manner such as locating tumors in each hemisphere and then comparing the two hemispheres to determine which has fewer tumors. In another example, the hemispheres are compared with known data (e.g., hemispheres without any tumors), and the hemisphere that is less different than the known data is selected as the least-tumor hemisphere. In some embodiments, determining a least-tumor hemisphere includes determining a symmetric difference between the flair and T2 MRIs, in the step 402, since a tumor rarely happens completely symmetrically, then thresholding and union are performed, in the step 404, and the hemisphere which does not contain the center of mass is the least-tumor hemisphere. In some embodiments, fewer or additional steps are implemented. In some embodiments, the order of the steps is modified.

Figure 5:
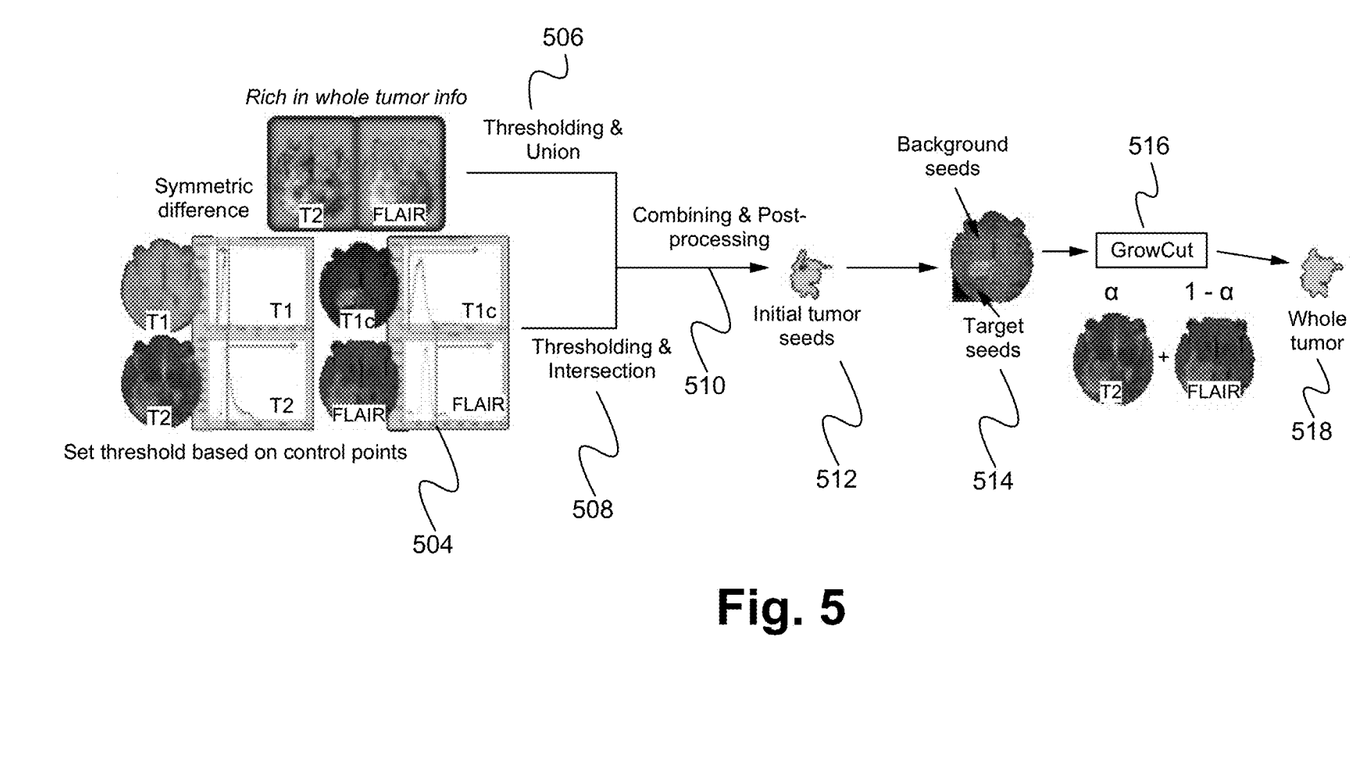
FIG. 5 illustrates a diagram of an initial tumor seeds locator and whole tumor segmentation algorithm according to some embodiments.

FIG. 5 illustrates a diagram of a whole tumor segmentation algorithm according to some embodiments. In the step 504, the intensity histogram for each of the multi-modal MRIs 300 (T1, T1c, Flair, T2) is analyzed, and thresholds are set based on control points and the symmetric difference of T2 and Flair are calculated. In the step 506, thresholding and union is implemented, and in the step 508, thresholding and intersection is implemented. In some embodiments, thresholding and union involves determining a threshold (e.g., based on statistics) and combining the different MRI images to form a union. In some embodiments, thresholding and intersection involves determining a threshold (e.g., based on control points) and determining when the different MRI images (e.g., intensity) intersect. The results are combined and then post-processing occurs in the step 510 to determine initial tumor seeds 512. Using the initial tumor seeds 512, background seeds and target seeds 514 are identified and used in the GrowCut (or another) algorithm 516 to determine a whole tumor 518. In some embodiments, fewer or additional steps are implemented. In some embodiments, the order of the steps is modified.

Figure 6:
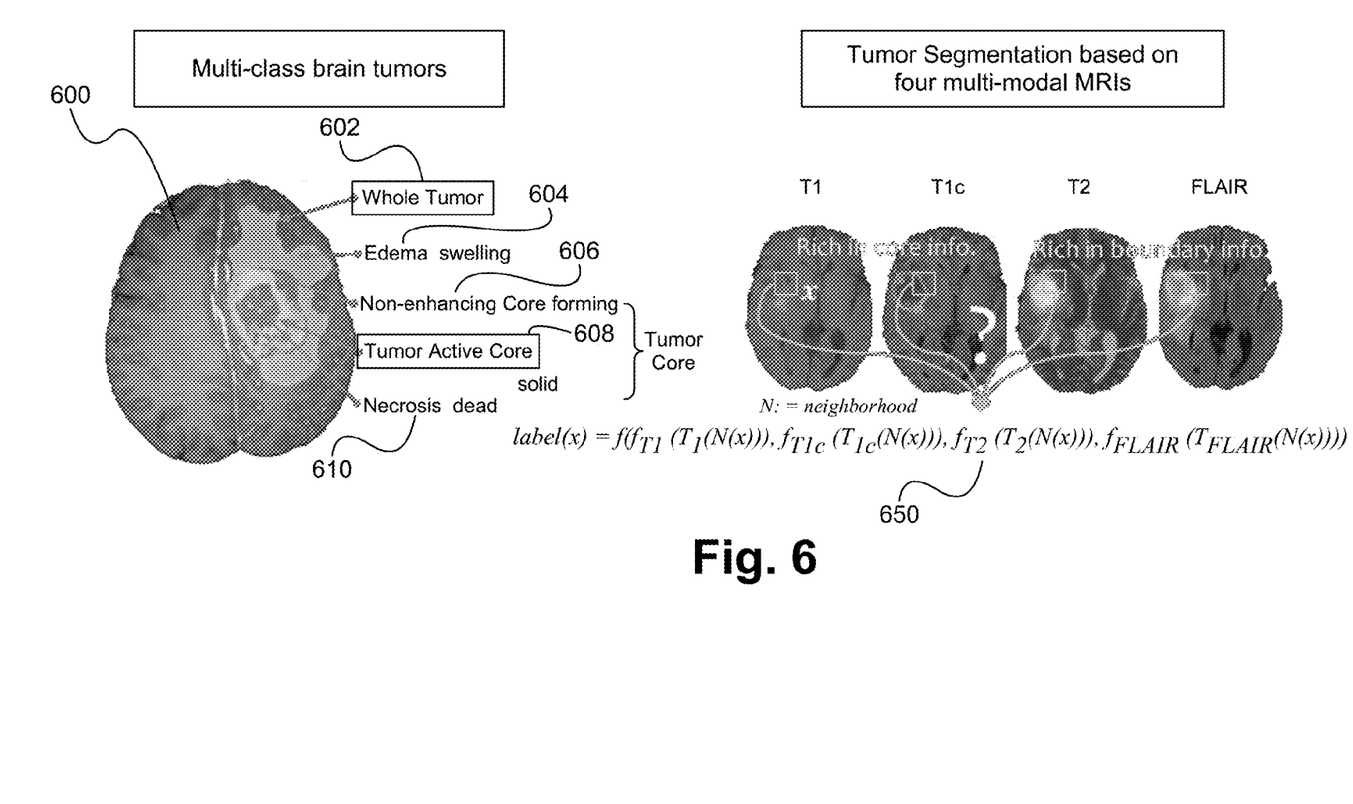
FIG. 6 illustrates a diagram of multi-class brain tumor segmentation challenges.

FIG. 6 illustrates a diagram of multi-class brain tumor segmentation challenges. The brain 600 includes a whole tumor 602, edema 604, non-enhancing core 606, an active core 608, and necrosis 610. The diagram 650 shows an exemplary formula for modeling complex medical decisions based on appearance and pathology rules.

Figure 7:
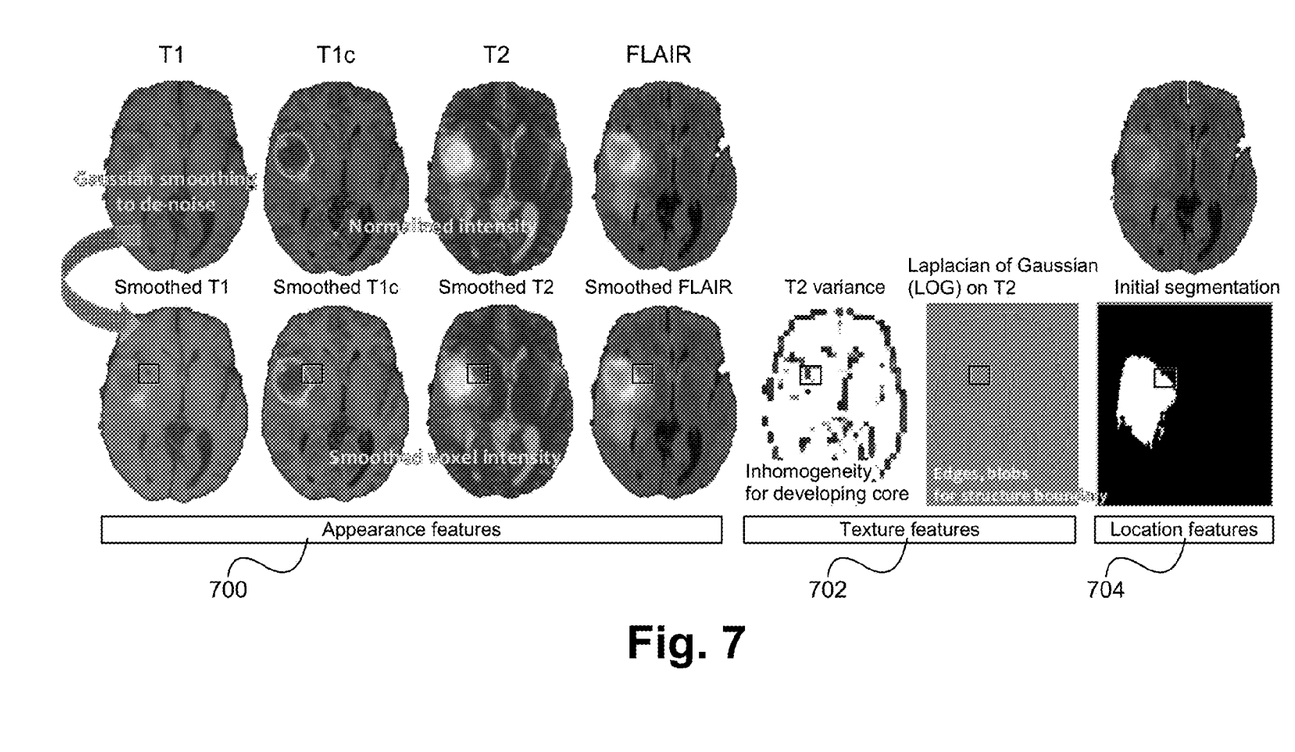
FIG. 7 illustrates a diagram of voxel-wise features for machine learning according to some embodiments.

FIG. 7 illustrates a diagram of voxel-wise features for machine learning according to some embodiments. The features include appearance features 700, texture features 702, and location features 704. The appearance features 700 are able to be determined by smoothing (e.g., Gaussian smoothing) to de-noise the MRIs. In some embodiments, the smoothing is applied to the MRIs after the intensity is normalized, such that the result is a smoothed voxel intensity. The texture features 702 are able to be analyzed using T2 variance to determine inhomogeneity for a develop core and a Laplacian of Gaussian (LOG) on T2 to determine edges and blobs for structure boundary. The location features 704 are also able to be analyzed based on the initial segmentation of the whole tumor.

Figure 8:
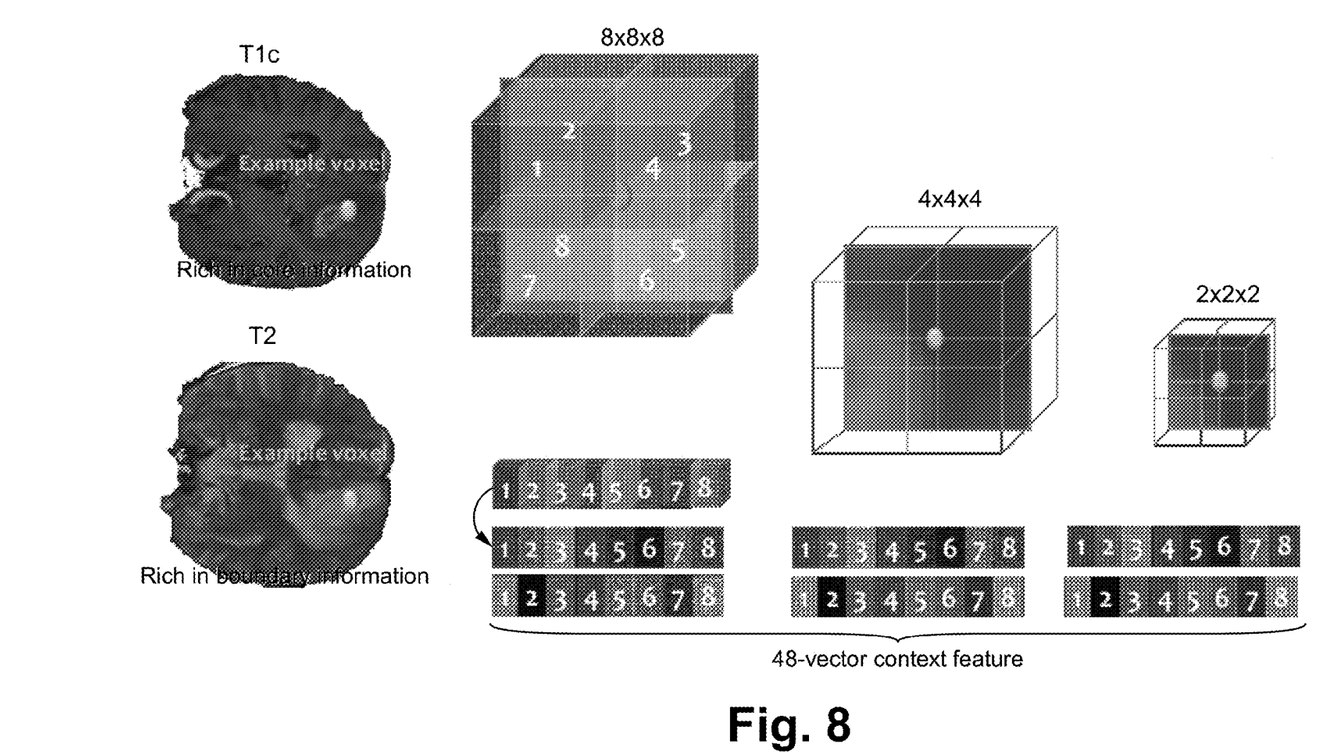
FIG. 8 illustrates a diagram of utilizing neighborhood information as context features according to some embodiments.

FIG. 8 illustrates a diagram of utilizing neighborhood information as context features according to some embodiments. The T1c MRI is rich in core information, and the T2 MRI is rich in boundary interformation. Thus, using the T1c and T2 MRIs, the mean intensity is extracted in each octant, multiscale context features are extracted, and the context features from T1c and T2 are combined.

Figure 9:
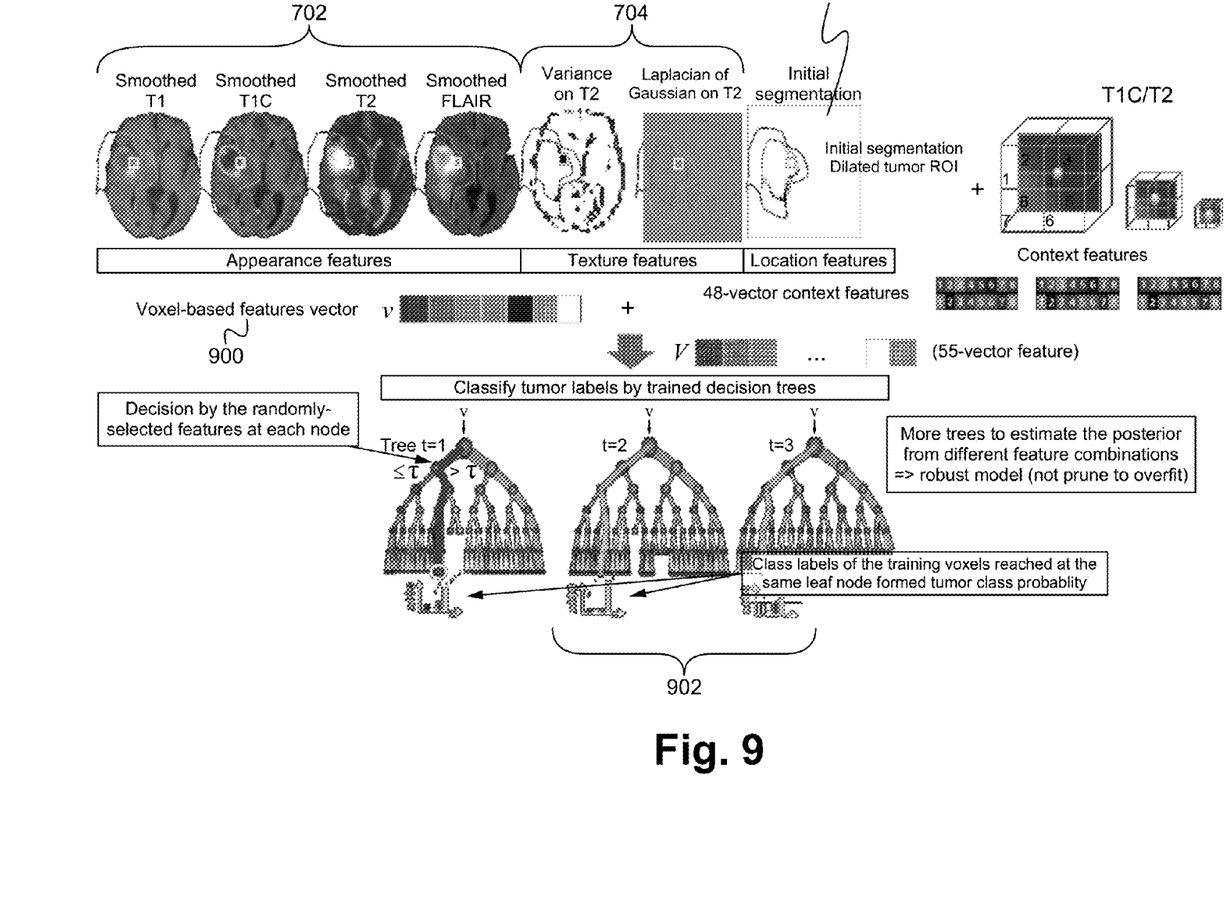
FIG. 9 illustrates a diagram of Random Forest classification according to some embodiments.

FIG. 9 illustrates a diagram of Random Forest classification according to some embodiments. Using the appearance features 702, texture features 704 and location features 706, a voxel-based feature vector 900 is generated which is combined with context features, and then trained decision trees 902 are able to classify the tumor labels.

Figure 10:
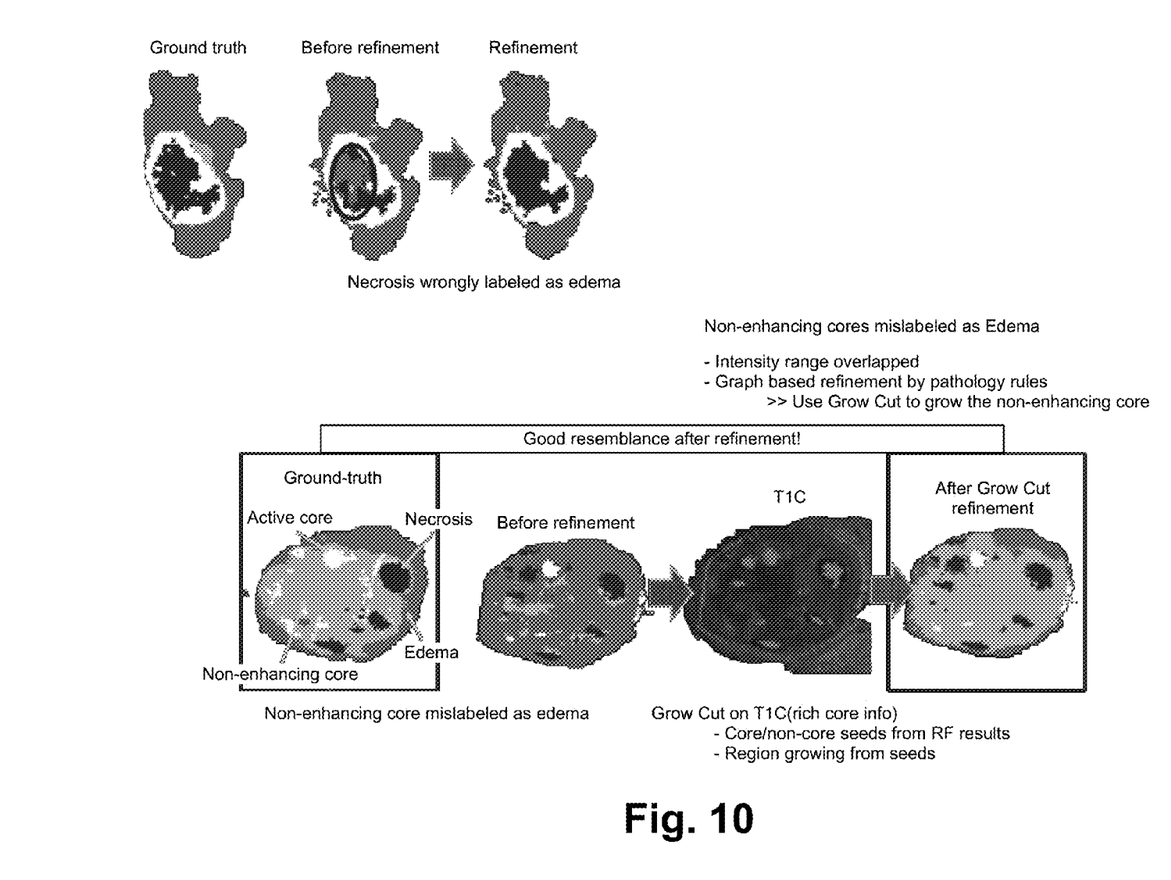
FIG. 10 illustrates a diagram of pathology-guided refinement according to some embodiments.

FIG. 10 illustrates a diagram of pathology-guided refinement according to some embodiments. To avoid items being mislabeled such as necrosis mislabeled as edema, or non-enhancing cores mislabeled as edema, pathology-guided refinement is utilized. For example, using context-based refinement or graph-based refinement based on pathology rules (e.g., using GrowCut to grow a non-enhancing core), the analysis is able to be refined to determine an accurate result.

Figure 11:
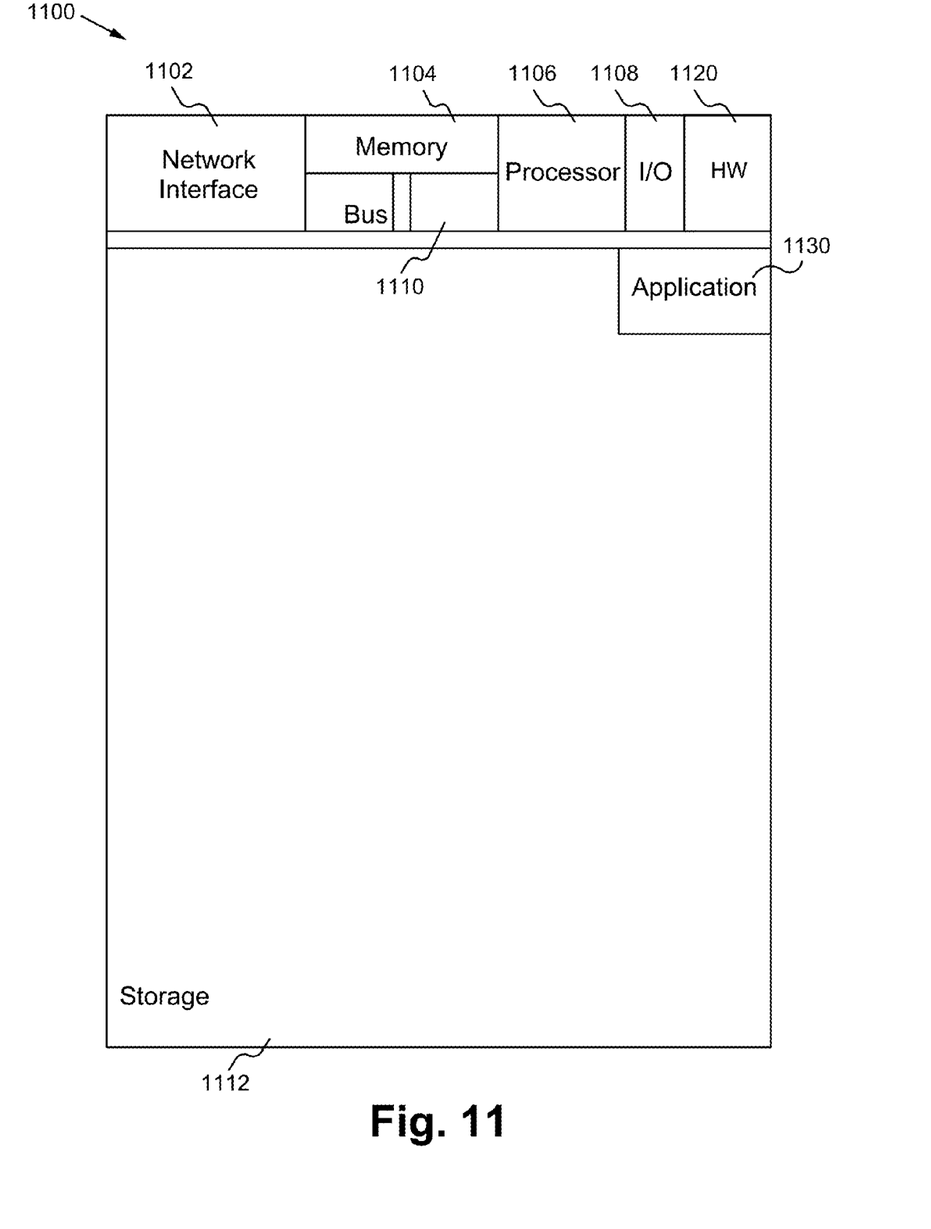
FIG. 11 illustrates a block diagram of an exemplary computing device configured to implement the automatic 3D brain tumor segmentation and classification method according to some embodiments.

FIG. 11 illustrates a block diagram of an exemplary computing device configured to implement the automatic 3D brain tumor segmentation and classification method according to some embodiments. The computing device 1100 is able to be used to acquire, store, compute, process, communicate and/or display information such as images and videos. In general, a hardware structure suitable for implementing the computing device 1100 includes a network interface 1102, a memory 1104, a processor 1106, I/O device(s) 1108, a bus 1110 and a storage device 1112. The choice of processor is not critical as long as a suitable processor with sufficient speed is chosen. The memory 1104 is able to be any conventional computer memory known in the art. The storage device 1112 is able to include a hard drive, CDROM, CDRW, DVD, DVDRW, High Definition disc/drive, ultra-HD drive, flash memory card or any other storage device. The computing device 1100 is able to include one or more network interfaces 1102. An example of a network interface includes a network card connected to an Ethernet or other type of LAN. The I/O device(s) 1108 are able to include one or more of the following: keyboard, mouse, monitor, screen, printer, modem, touchscreen, button interface and other devices. Automatic 3D brain tumor segmentation and classification application(s) 1130 used to perform the automatic 3D brain tumor segmentation and classification method are likely to be stored in the storage device 1112 and memory 1104 and processed as applications are typically processed. More or fewer components shown in FIG. 11 are able to be included in the computing device 1100. In some embodiments, automatic 3D brain tumor segmentation and classification method hardware 1120 is included. Although the computing device 1100 in FIG. 11 includes applications 1130 and hardware 1120 for the automatic 3D brain tumor segmentation and classification method, the automatic 3D brain tumor segmentation and classification method is able to be implemented on a computing device in hardware, firmware, software or any combination thereof. For example, in some embodiments, the automatic 3D brain tumor segmentation and classification method applications 1130 are programmed in a memory and executed using a processor. In another example, in some embodiments, the automatic 3D brain tumor segmentation and classification method hardware 1120 is programmed hardware logic including gates specifically designed to implement the automatic 3D brain tumor segmentation and classification method.

In some embodiments, the automatic 3D brain tumor segmentation and classification method application(s) 1130 include several applications and/or modules. In some embodiments, modules include one or more sub-modules as well. In some embodiments, fewer or additional modules are able to be included.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, a home entertainment system, an augmented reality device, a virtual reality device, smart jewelry (e.g., smart watch) or any other suitable computing device.

Figure 12:
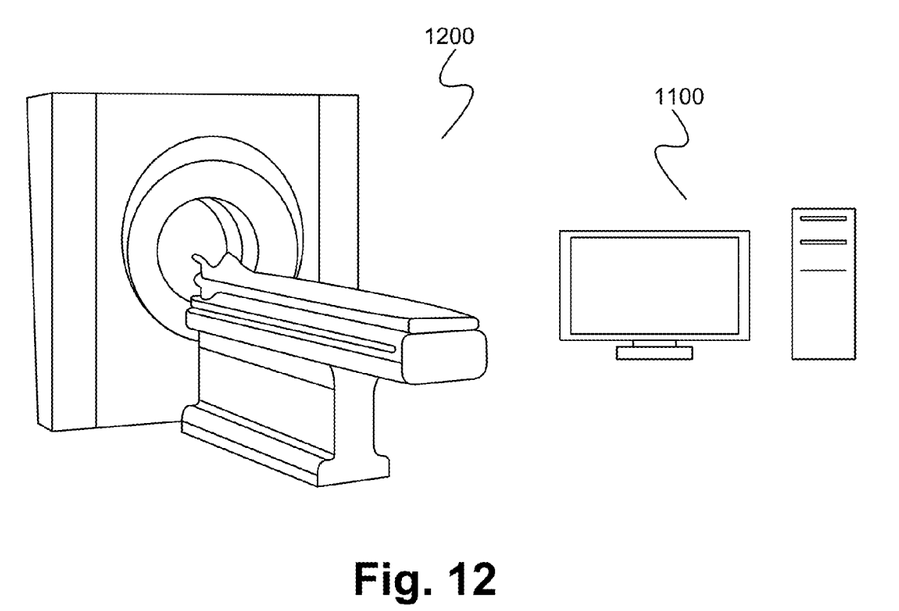
FIG. 12 illustrates a diagram of a Magnetic Resonance Imaging (MRI) system according to some embodiments.

FIG. 12 illustrates a diagram of a Magnetic Resonance Imaging (MRI) system according to some embodiments. An MRI device 1200 is used to acquire MRI images such as brain scans. A computing device 1100 receives the MRI information (e.g., by downloading or accessing in the cloud) from the MRI device 1200, and the computing device 1100 performs the automatic 3D brain tumor segmentation and classification method.

To utilize the automatic 3D brain tumor segmentation and classification method described herein, MRI information is analyzed using the automatic 3D brain tumor segmentation and classification method. Based upon the analysis, tumors are able to be identified. Based upon the identified tumors, surgeons are able to perform operations to remove the tumors.

In operation, the automatic 3D brain tumor segmentation and classification method efficiently and accurately identifies tumors in MRI information without user input.

Although the automatic 3D brain tumor segmentation and classification has been described herein related to brain tumors, the automatic 3D brain tumor segmentation and classification method is able to be adapted for any other tumors or maladies.

Some Embodiments of Automatic 3D Brain Tumor Segmentation and Classification

1. A method programmed in a non-transitory memory of a device comprising:
   performing whole tumor segmentation; and
   performing multi-class tumor segmentation.
2. The method of clause 1 wherein the whole tumor segmentation includes: data normalization and initial segmentation.
3. The method of clause 1 wherein the whole tumor segmentation includes:
   utilizing multi-modal MRIs including T1, T1c, Flair and T2;
   determining a least-tumor hemisphere;
   classifying tissue;

identifying intensity control points based on intensities of different tissue structures;
normalizing the intensity for each of the MRIs based on the intensity control points;
locating initial tumor seeds; and
segmenting a tumor based on the tumor seeds.
4. The method of clause 1 wherein the multi-class tumor segmentation includes: feature extraction, voxel classification and refinement.
5. The method of clause 4 wherein feature extraction includes: determining voxel-wise features and context features, wherein voxel-wise features include appearance features, texture features and location features.
6. The method of clause 5 wherein context feature extraction further includes: extracting a mean intensity in each octant of an MRI, extracting multiscale context features and combining the context features from a T1c MRI and a T2 MRI.
7. The method of clause 6 wherein voxel classification utilizes information from the feature extraction and decision trees to classify a tumor.
8. The method of clause 7 wherein refinement includes pathology-guided refinement to ensure a correct classification of the tumor.
9. An apparatus comprising:
a non-transitory memory for storing an application, the application for:
performing whole tumor segmentation; and
performing multi-class tumor segmentation; and
a processing component coupled to the memory, the processing component configured for processing the application.
10. The apparatus of clause 9 wherein the whole tumor segmentation includes: data normalization and initial segmentation.
11. The apparatus of clause 9 wherein the whole tumor segmentation includes:
utilizing multi-modal MRIs including T1, T1c, Flair and T2;
determining a least-tumor hemisphere;
classifying tissue;
identifying intensity control points based on intensities of different tissue structures;
normalizing the intensity for each of the MRIs based on the intensity control points;
locating initial tumor seeds; and
segmenting a tumor based on the tumor seeds.
12. The apparatus of clause 9 wherein the multi-class tumor segmentation includes: feature extraction, voxel classification and refinement.
13. The apparatus of clause 12 wherein feature extraction includes: voxel-wise features and context features, wherein voxel-wise features include determining appearance features, texture features and location features.
14. The apparatus of clause 13 wherein context feature extraction further includes: extracting a mean intensity in each octant of an MRI, extracting multiscale context features and combining the context features from a T1c MRI and a T2 MRI.
15. The apparatus of clause 14 wherein voxel classification utilizes information from the feature extraction and decision trees to classify a tumor.
16. The apparatus of clause 15 wherein refinement includes pathology-guided refinement to ensure a correct classification of the tumor.
17. A system comprising:
a magnetic resonance imaging device; and
a computing device configured for:
performing whole tumor segmentation; and
performing multi-class tumor segmentation.
18. The system of clause 17 wherein the whole tumor segmentation includes: data normalization and initial segmentation.
19. The system of clause 17 wherein the whole tumor segmentation includes:
utilizing multi-modal MRIs including T1, T1c, Flair and T2;
determining a least-tumor hemisphere;
classifying tissue;
identifying intensity control points based on intensities of different tissue structures;
normalizing the intensity for each of the MRIs based on the intensity control points;
locating initial tumor seeds; and
segmenting a tumor based on the tumor seeds.
20. The system of clause 17 wherein the multi-class tumor segmentation includes: feature extraction, voxel classification and refinement.
21. The system of clause 20 wherein feature extraction includes: voxel-wise features and context features, wherein voxel-wise features include determining appearance features, texture features and location features.
22. The system of clause 21 wherein context feature extraction further includes: extracting a mean intensity in each octant of an MRI, extracting multiscale context features and combining the context features from a T1c MRI and a T2 MRI.
23. The system of clause 22 wherein voxel classification utilizes information from the feature extraction and decision trees to classify a tumor.
24. The system of clause 23 wherein refinement includes pathology-guided refinement to ensure a correct classification of the tumor.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:
1. A method programmed in a non-transitory memory of a device comprising:
performing whole tumor segmentation, wherein the whole tumor segmentation includes:
utilizing multi-modal MRIs including T1, T1c, Flair and T2;
determining a least-tumor hemisphere;
classifying tissue;
identifying intensity control points based on intensities of different tissue structures;
normalizing the intensity for each of the MRIs based on the intensity control points;
locating initial tumor seeds; and
segmenting a tumor based on the tumor seeds; and
performing multi-class tumor segmentation.
2. The method of claim 1 wherein the whole tumor segmentation includes: data normalization and initial segmentation.

3. The method of claim 1 wherein the multi-class tumor segmentation includes: feature extraction, voxel classification and refinement.

4. The method of claim 3 wherein feature extraction includes: determining voxel-wise features and context features, wherein voxel-wise features include appearance features, texture features and location features.

5. The method of claim 4 wherein context feature extraction further includes: extracting a mean intensity in each octant of an MRI, extracting multiscale context features and combining the context features from a T1c MRI and a T2 MRI.

6. The method of claim 5 wherein voxel classification utilizes information from the feature extraction and decision trees to classify a tumor.

7. The method of claim 6 wherein refinement includes pathology-guided refinement to ensure a correct classification of the tumor.

8. An apparatus comprising:
a non-transitory memory for storing an application, the application for:
performing whole tumor segmentation, wherein the whole tumor segmentation includes:
utilizing multi-modal MRIs including T1, T1c, Flair and T2;
determining a least-tumor hemisphere;
classifying tissue;
identifying intensity control points based on intensities of different tissue structures;
normalizing the intensity for each of the MRIs based on the intensity control points;
locating initial tumor seeds; and
segmenting a tumor based on the tumor seeds; and
performing multi-class tumor segmentation; and
a processing component coupled to the memory, the processing component configured for processing the application.

9. The apparatus of claim 8 wherein the whole tumor segmentation includes: data normalization and initial segmentation.

10. The apparatus of claim 8 wherein the multi-class tumor segmentation includes: feature extraction, voxel classification and refinement.

11. The apparatus of claim 10 wherein feature extraction includes: voxel-wise features and context features, wherein voxel-wise features include determining appearance features, texture features and location features.

12. The apparatus of claim 11 wherein context feature extraction further includes: extracting a mean intensity in each octant of an MRI, extracting multiscale context features and combining the context features from a T1c MRI and a T2 MRI.

13. The apparatus of claim 12 wherein voxel classification utilizes information from the feature extraction and decision trees to classify a tumor.

14. The apparatus of claim 13 wherein refinement includes pathology-guided refinement to ensure a correct classification of the tumor.

15. A system comprising:
a magnetic resonance imaging device; and
a computing device configured for:
performing whole tumor segmentation, wherein the whole tumor segmentation includes:
utilizing multi-modal MRIs including T1, T1c, Flair and T2;
determining a least-tumor hemisphere;
classifying tissue;
identifying intensity control points based on intensities of different tissue structures:
normalizing the intensity for each of the MRIs based on the intensity control points;
locating initial tumor seeds; and
segmenting a tumor based on the tumor seeds; and
performing multi-class tumor segmentation.

16. The system of claim 15 wherein the whole tumor segmentation includes: data normalization and initial segmentation.

17. The system of claim 15 wherein the multi-class tumor segmentation includes: feature extraction, voxel classification and refinement.

18. The system of claim 17 wherein feature extraction includes: voxel-wise features and context features, wherein voxel-wise features include determining appearance features, texture features and location features.

19. The system of claim 18 wherein context feature extraction further includes: extracting a mean intensity in each octant of an MRI, extracting multiscale context features and combining the context features from a T1c MRI and a T2 MRI.

20. The system of claim 19 wherein voxel classification utilizes information from the feature extraction and decision trees to classify a tumor.

21. The system of claim 20 wherein refinement includes pathology-guided refinement to ensure a correct classification of the tumor.

22. A method programmed in a non-transitory memory of a device comprising:
performing whole tumor segmentation; and
performing multi-class tumor segmentation, wherein the multi-class tumor segmentation includes: feature extraction, voxel classification and refinement, wherein feature extraction includes: determining voxel-wise features and context features, wherein voxel-wise features include appearance features, texture features and location features, wherein context feature extraction further includes: extracting a mean intensity in each octant of an MRI, extracting multiscale context features and combining the context features from a T1c MRI and a T2 MRI.

23. The method of claim 22 wherein the whole tumor segmentation includes: data normalization and initial segmentation.

24. The method of claim 22 wherein voxel classification utilizes information from the feature extraction and decision trees to classify a tumor.

25. The method of claim 24 wherein refinement includes pathology-guided refinement to ensure a correct classification of the tumor.

26. An apparatus comprising:
a non-transitory memory for storing an application, the application for:
performing whole tumor segmentation; and
performing multi-class tumor segmentation, wherein the multi-class tumor segmentation includes: feature extraction, voxel classification and refinement, wherein feature extraction includes: determining voxel-wise features and context features, wherein voxel-wise features include appearance features, texture features and location features, wherein context feature extraction further includes: extracting a mean intensity in each octant of an MRI, extracting multiscale context features and combining the context features from a T1c MRI and a T2 MRI; and a processing component coupled to the memory, the processing component configured for processing the application.

27. The apparatus of claim 26 wherein the whole tumor segmentation includes: data normalization and initial segmentation.

28. The apparatus of claim 26 wherein voxel classification utilizes information from the feature extraction and decision trees to classify a tumor.

29. The apparatus of claim 28 wherein refinement includes pathology-guided refinement to ensure a correct classification of the tumor.

* * * * *